United States Patent [19]
Jones

[11] Patent Number: 6,044,351
[45] Date of Patent: Mar. 28, 2000

[54] MINIMUM INCOME PROBABILITY DISTRIBUTION PREDICTOR FOR HEALTH CARE FACILITIES

[76] Inventor: Annie M. W. Jones, 1081 Mindingall Rd., Tuskegee, Ala. 36083

[21] Appl. No.: 08/993,672

[22] Filed: Dec. 18, 1997

[51] Int. Cl.$^7$ ............................................. G06F 17/60
[52] U.S. Cl. ...................... 705/2; 705/3; 705/8; 705/10
[58] Field of Search ................................ 705/2, 3, 8, 10, 705/22, 35

[56] References Cited

U.S. PATENT DOCUMENTS

| | | | |
|---|---|---|---|
| 5,018,067 | 5/1991 | Mohlenbrock et al. | 600/300 |
| 5,065,315 | 11/1991 | Garcia | 364/413.01 |
| 5,070,452 | 12/1991 | Doyle, Jr. et al. | 705/2 |
| 5,307,262 | 4/1994 | Ertel | 705/2 |
| 5,324,077 | 6/1994 | Kessler et al. | 283/54 |
| 5,325,293 | 6/1994 | Dorne | 364/413.01 |
| 5,365,425 | 11/1994 | Torma et al. | 705/2 |
| 5,461,699 | 10/1995 | Arbabi et al. | 706/21 |
| 5,557,514 | 9/1996 | Seare et al. | 705/2 |
| 5,596,493 | 1/1997 | Tone et al. | 705/10 |
| 5,615,109 | 3/1997 | Eder | 705/8 |
| 5,778,345 | 7/1998 | McCartney | 705/2 |

OTHER PUBLICATIONS

Unison Technology Inc., Unison Technology Unveils Predict! (TM) A Breakthrough in Decision Support Software, Dialog File 621:IAC New Product Announcement, pp. 1–2, Feb. 2, 1987.

Medirisk, Inc., Medirisk, Inc. Introduces Fee Manager for Windows, Dialog File 649:IAC Newswire ASAP, pp. 1–2, Sep. 16, 1996.

*Primary Examiner*—Emanuel Todd Voeltz
*Assistant Examiner*—John W. Hayes

[57] ABSTRACT

A computer program, PREdictor of Minimum INcome (PREMIN), has been developed for predicting health care facility future minimum income (FMI). PREMIN was developed using "MICROSOFT" "EXCEL" for "WINDOWS" 4.0. PREMIN allows estimation of anticipated number of office visits with three values, L (least possible), M (most probable), and H (most possible), and speculation of proportion of payments sources, i.e. HMO's Medicare, Medicaid, etc. The mathematical and statistical foundation of PREMIN is based on a method that determines the minimum number of independently distributed random variables required in a linear combination in order that its distribution can be approximated by the normal density function.

Number of office visits are treated as a random variable and are approximated by the triangular distribution. Proportion of payment data is used to compute coefficients in linear combinations. If normal approximation is not adequate, PREMIN simulates the FMI distribution based on the input data. Therefore, PREMIN output is, in some cases, a plot of the normal probability density function for a FMI distribution and associated cumulative probabilities. PREMIN output may also be a histogram of simulated FMI values and associated summary statistics such as a frequency distribution by count and percentages.

PREMIN provides a useful tool to estimate the distribution of FMI. After several demonstrations of the program to health care professionals, it is concluded that current methods of predicting income are quite immature in comparison with probabilistic calculations utilized by PREMIN. Further, the computer system can provide vital and beneficial financial data to health care facilities.

3 Claims, 30 Drawing Sheets

Patient Classification And Base Charge

Enter a single patient classification, i.e., age group, type of illness, etc.
Patient Classification [                              ]

The base office visit charge should not include the cost of any medical procedures that may occur during the visit.
Base Office Visit Charge ($) [          ]

Figure 2D

Total Time Periods

Value must be for equal length time periods, i.e. all days, all weeks, and must be integer. The maximum number of time is 60.

Enter total number of time periods

Figure 2E

Office Visits

This input must be integer

Note:  L<M<H  or  L=M<H  or  L<M=H

L = smallest possible  ☐

M = most probable  ☐

H = largest possible  ☐

Figure 2F

Source of Payment Proportions and Additional Data

Enter proportions (decimal) in column 1. All dollar amounts must be numeric. All HMO # patients must be integer.

FULL

Partial (1)   [0]   Dollar Amt.  [0]
Partial (1)   [0]   Dollar Amt.  [0]
Partial (1)   [0]   Dollar Amt.  [0]
Partial (1)   [0]   Dollar Amt.  [0]

HMO(1)   [0]   # Patients   [0]   Capitation $  [0]   Copay$  [0]
HMO(2)   [0]   # Patients   [0]   Capitation $  [0]   Copay$  [0]
HMO(3)   [0]   # Patients   [0]   Capitation $  [0]   Copay$  [0]
HMO(4)   [0]   # Patients   [0]   Capitation $  [0]   Copay$  [0]
HMO(5)   [0]   # Patients   [0]   Capitation $  [0]   Copay$  [0]

NONE:   [0]

Figure 2G

MINIMUM INCOME PROBABILITY DISTRIBUTION PREDICTOR FOR HEALTH CARE FACILITIES

BACKGROUND—FIELD OF INVENTION

This invention relates to predicting future minimum income, specifically income of health care facilities.

BACKGROUND—DESCRIPTION OF PRIOR ART

Computerized systems that predict health care facility future minimum income (FMI) are either nonexistent or have not been published or patented. Computerized systems do exist that provide financial estimations relative to health care facilities. However, the estimation provided are of little or no use to physicians who want to predict future minimum income. Knowledge of FMI can be valuable in a medical practice, particularly office and health care delivery planning. FMI can be viewed as the "worst case" scenario for physician income.

U.S. Pat. No. 5,018,067 to Mohlenbrock et al. (1991) relates to the identification of quality and cost efficient medical providers. It also relates to computer software techniques and systems for estimating cost to treat a patient. However, knowledge of cost without knowledge of income is of little use to a physician faced with decisions such as size of staff that can be afforded, purchase or lease options, and contractual agreements with insurance companies. U.S. Pat. No. 5,065,315 to Garcia (1991) relates to a computerized system located throughout the hospital facility for hospital medical record maintenance and scheduling system. However, this invention does not provide useful data to individual physicians about future minimum income. U.S. Pat. No. 5,070,452 to Doyle, Jr. et al. (1991) relates to a computerized system that included a comprehensive roster of all persons having insurance benefits available. The system included the particular medical treatment reimbursable by insurance and the dollar value of the reimbursement for each treatment. However, while the invention does generate a reimbursement amount, the invention does not generate predictions of future income for a physician. U.S. Pat. No. 5,307,262 to Ertel (1994) relates to a computerized system for reviewing the quality of patient data required on hospital payment claims. However, the invention does not relate to physician income. U.S. Pat. No. 5,325,077 to Kessler et al. (1994) relates to a system for gathering and evaluating data on delivery of medical care for ambulatory patient visits. However, primary focus of the invention is ensuring accurate and quality data on care being delivered to patients. Income received by physicians is related to individual patients after medical care is rendered. The invention does not address future income. U.S. Pat. No. 5,325,293 to Dorne (1994) relates to a system and a method for correlating medical procedures and medical billing codes. The computerized system translates medical procedures into accurate billing codes. It allows a physician to plan medical procedures in advance and modify planned procedures after performing the examination then automatically translates the performed procedures into billing codes. The billing codes do lead to specifying physician income, however, the invention does not address future income. U.S. Pat. No. 5,365,425 to Torma et al. (1994) relates to quality, cost and access in medical treatment. Medical care facilities can then be compared to each other and deficiencies identified. The invention does not address physician income. U.S. Pat. No. 5,557,514 To Seare et al. (1996) relates to a computerized system and method for analyzing healthcare providers billing patterns, enabling an assessment of medical services utilization patterns and determining whether a provider or multiple providers are over utilizing or under utilizing services when compared to a particular historical profile. The invention does not address physician income.

OBJECTS AND ADVANTAGES

Several objects and advantages of a minimum income probability distribution predictor for health care facilities are:

(a) to provide an interactive computerized method that predicts the probability distribution of health care facility future minimum income (FMI) for a total time interval (TTI) consisting of equal sized time subintervals (TSI);

(b) to allow estimation of anticipated number of ambulatory office visits with three values: least probable (L), most probable (M), and most possible (H);

(c) to allow speculation of proportion of payment services, i.e., health maintenance organizations (HMO), Medicare, Medicaid, etc.;

(d) to provide a plot of the normal probability density function for a future minimum income distribution and associated cumulative probabilities, when applicable;

(e) to provide a histogram of simulated FMI values and associated summary statistics such as a frequency distribution by count and percentages when applicable.

Further objects and advantages are to provide physicians strategies regarding health care facility management decisions such as:

(1) Size of staff that can be afforded
(2) Purchase or lease options and other expenses
(3) Practice arrangements such as solo, partnership, or group
(4) Contractual agreements with insurance companies
(5) Fee changes
(6) Investments to be made
(7) Retirement

DRAWING FIGURES

In the drawings, closely related figures have the same number but different alphabetic suffixes.

REFERENCE NUMERALS IN DRAWINGS

10 START
12 Number of Time Periods (TTI)
14 Patient Classification
16 Base Office Visit Charge
18 Three Parameter Values for Number of Office Visits
20 Source of Payment Proportions and Payment Amounts
22 Minimum Income Constants
24 Moments for Number of Office Visits Distribution at each TSI 26 FMI Linear Combination
28 Minimum Number of Independently Distributed Random Variables for Normal Approximation
30 Normal Approximation Adequate?
32 Monte Carlo Simulation of k Number of Office Visits for Each TSI
34 FMI Calculations
36 FMI Distribution
38 Simulated FMI Distribution (Histogram)
40 interval Probabilities Etc.
42 STOP

SUMMARY

The minimum income probability distribution predictor for health care facilities comprises a prototypes interactive computer system (PREMIN—PREdictor of Minimum INcome) that will provide a system user with capability of specifying input data that will then be used to predict future minimum income (FMI).

System users are envisioned as being physicians or affiliated health care personnel interested in predicting or need to predict FMI for a specified total time interval, TTI.

The system is easy to use, and is capable of conveniently and quickly generating FMI information that can assist in health care planning and analysis. The interactive computer program advantageously embodies the invention method. The interactive program desirably runs in a standard AT compatible 80486 computer platform, or the like, and operates in a "MICROSOFT" "WINDOWS" graphic environment. The computer system is designed and coded using "MICROSOFT" "WINDOWS" "EXCEL" version 4.0 macro commands. "EXCEL" is transportable to other computers and "EXCEL" macro commands simplify program coding.

Description—FIG. 2

Figure 2A:
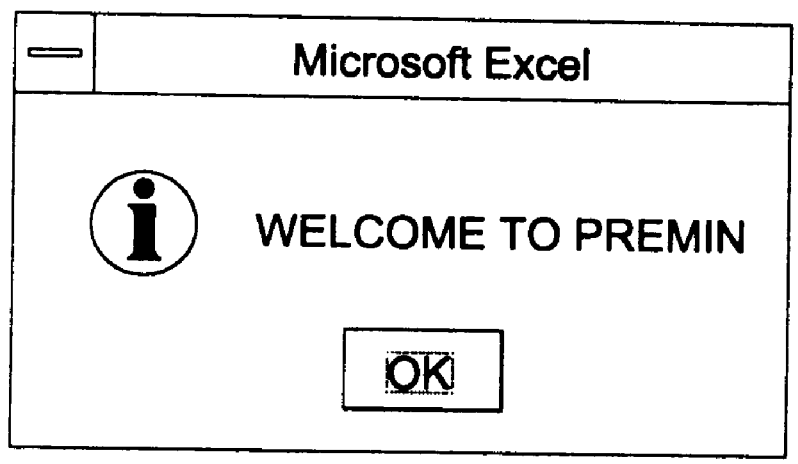
FIGS. 2A to 2R show the screen-by-screen, as seen on a computer monitor, aspects of the computerized FMI prediction system.
Figure 2B:
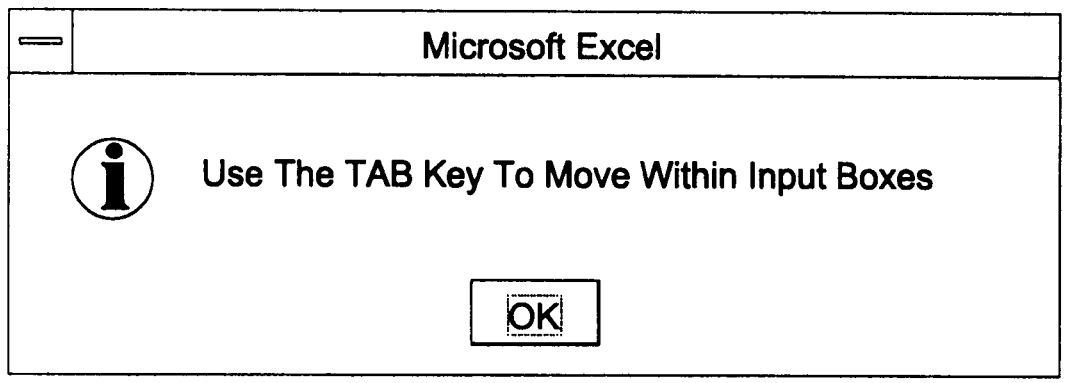
Figure 2C:
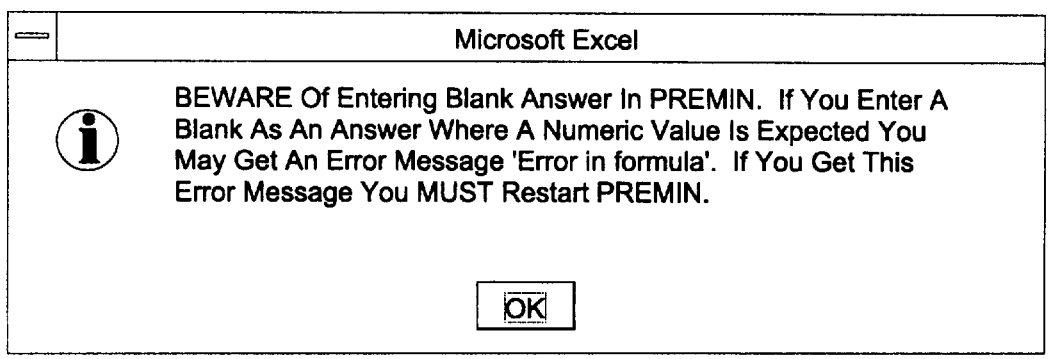
Figure 2H:
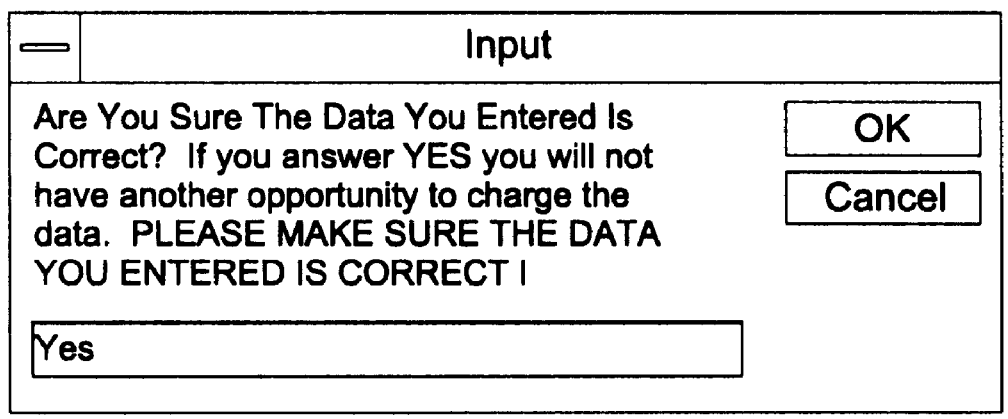
Figure 2I:
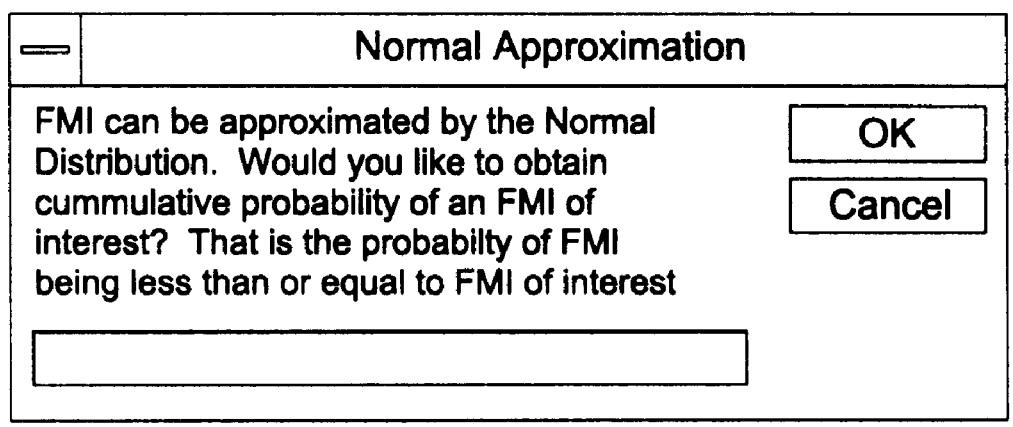
Figure 2J:
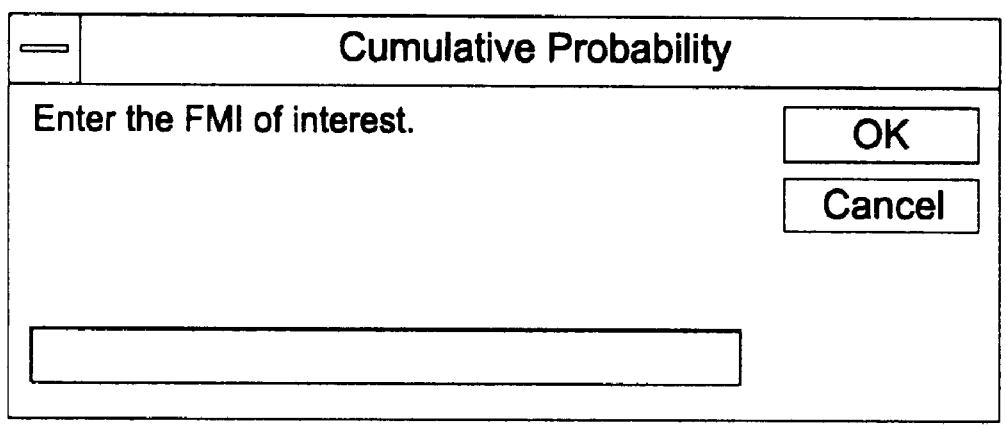
Figure 2K:
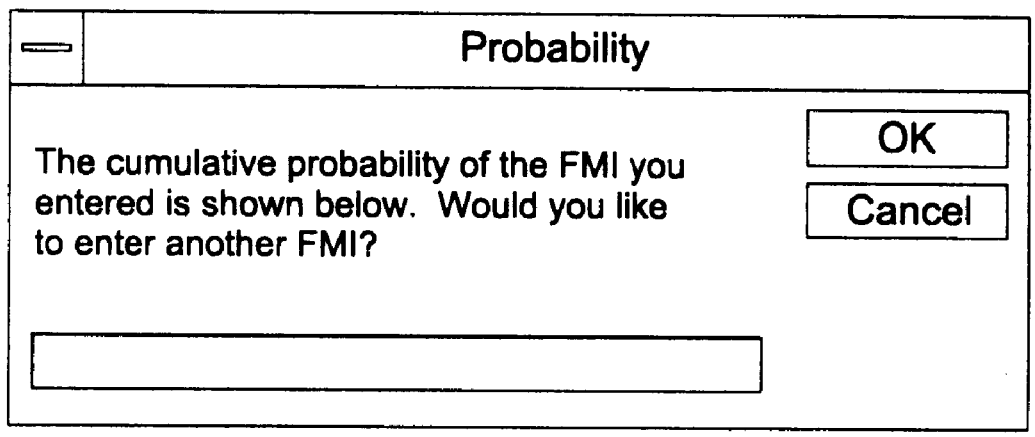
Figure 2L:
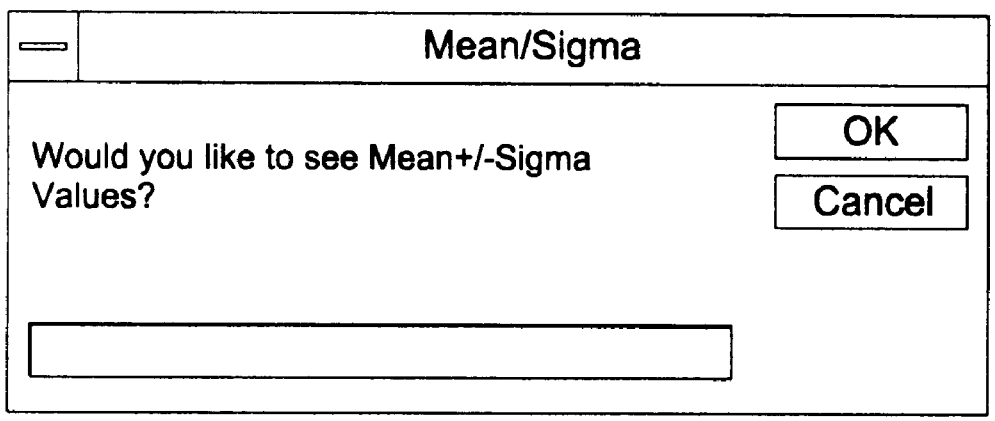
Figure 2M:
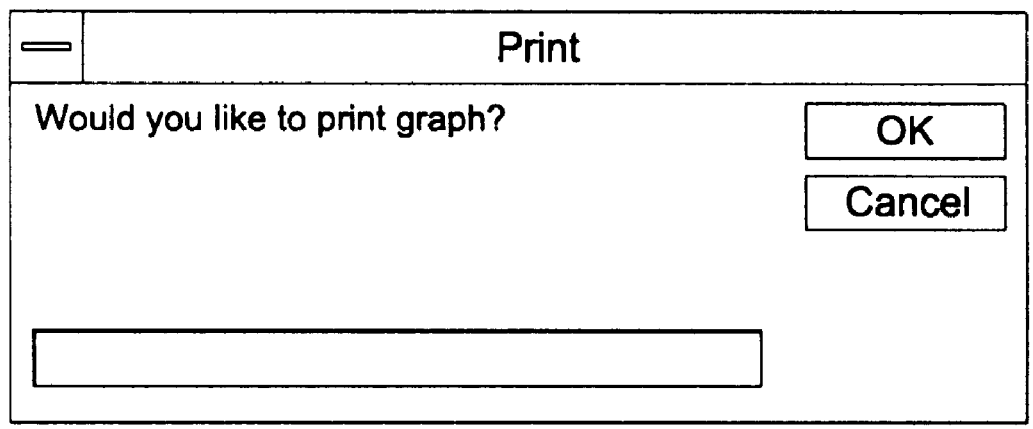
Figure 2N:
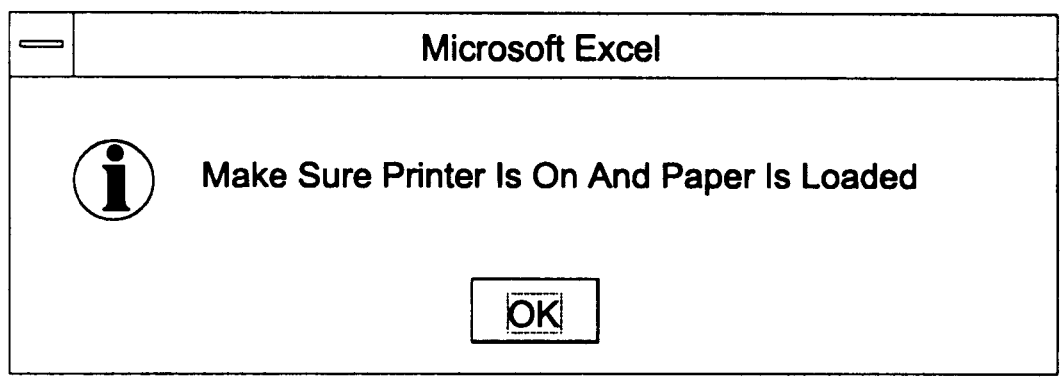
Figure 20:
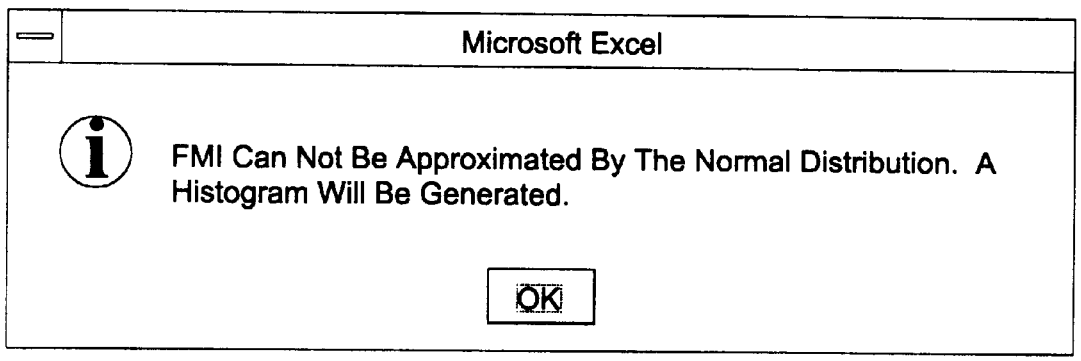
Figure 2P:
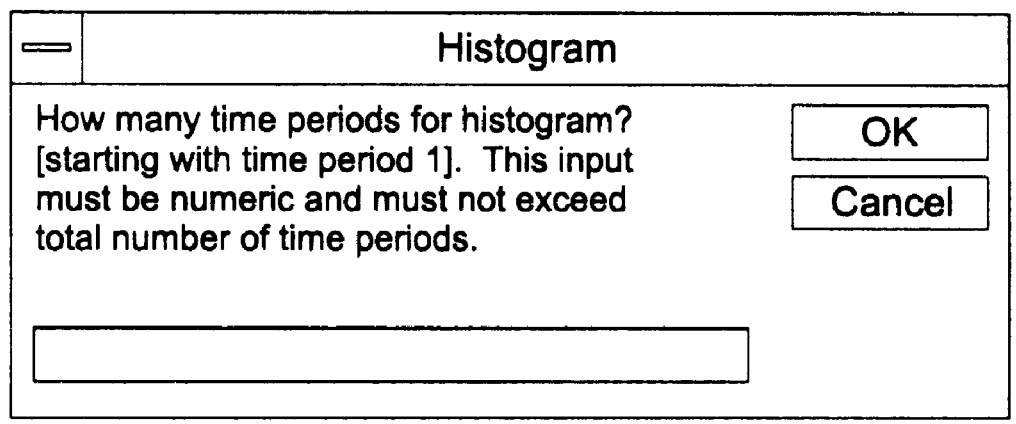
Figure 2Q:
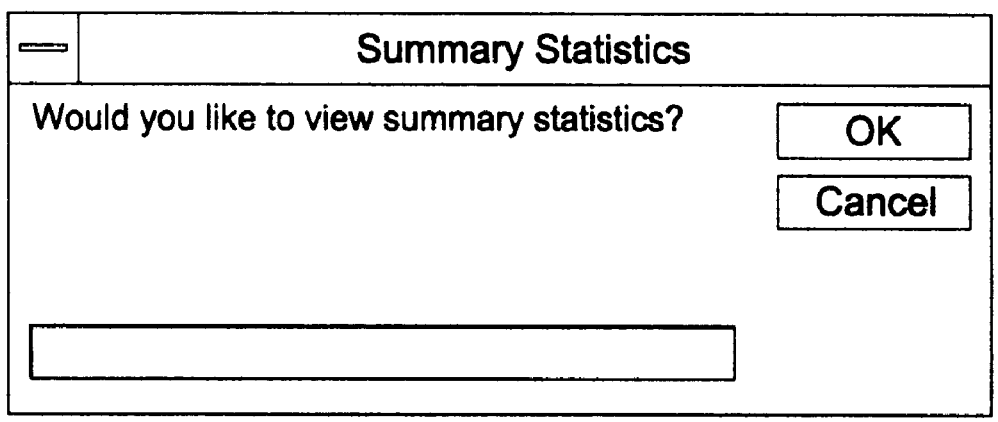
Figure 2R:
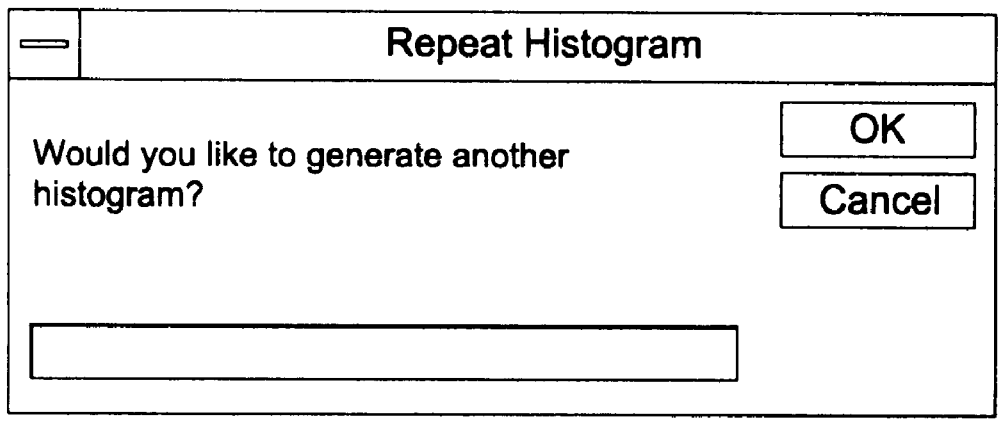
Figure 3A:
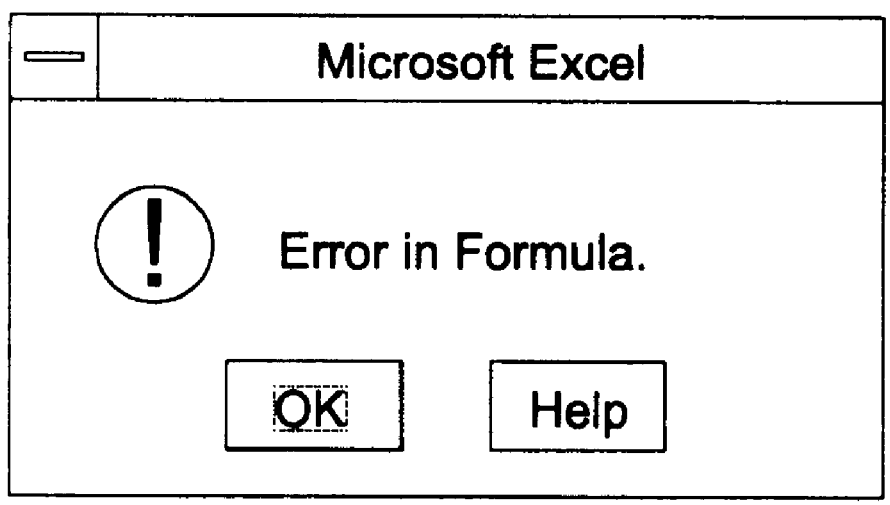
FIGS. 3A to 3I show the screen error messages, as seen on a computer monitor, of the computerized FMI prediction system.
Figure 3B:
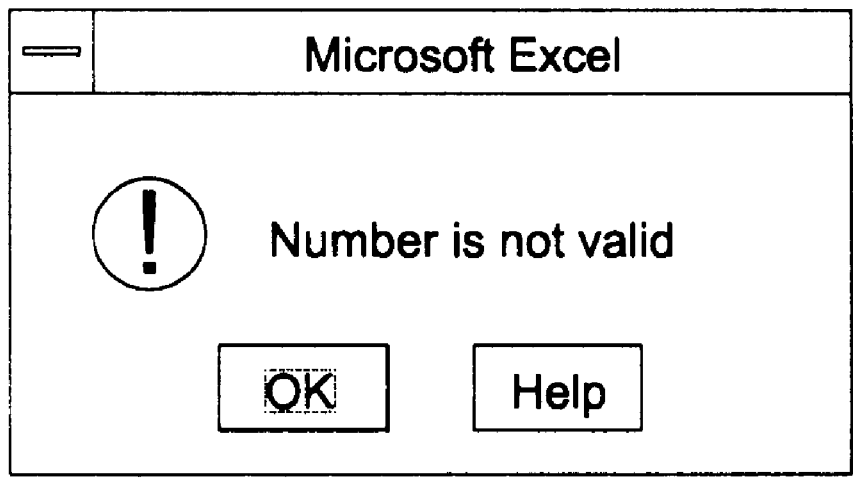
Figure 3C:
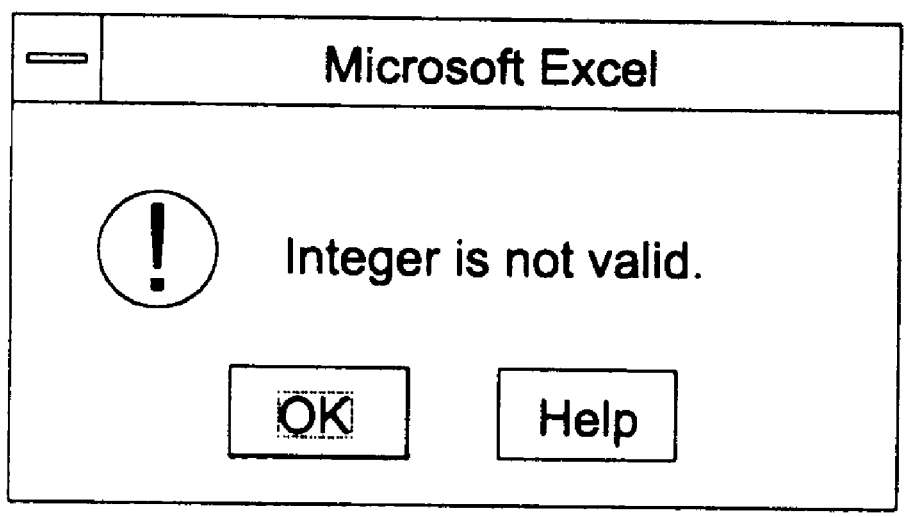
Figure 3D:
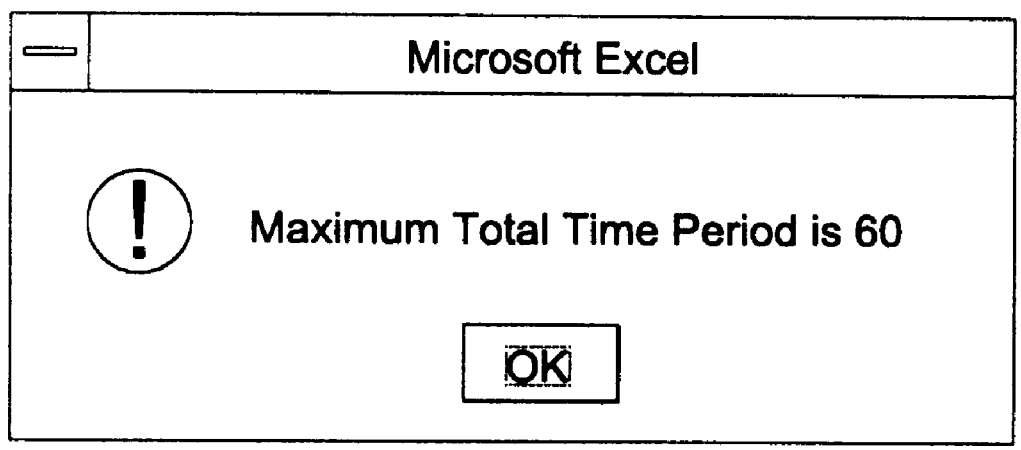
Figure 3E:
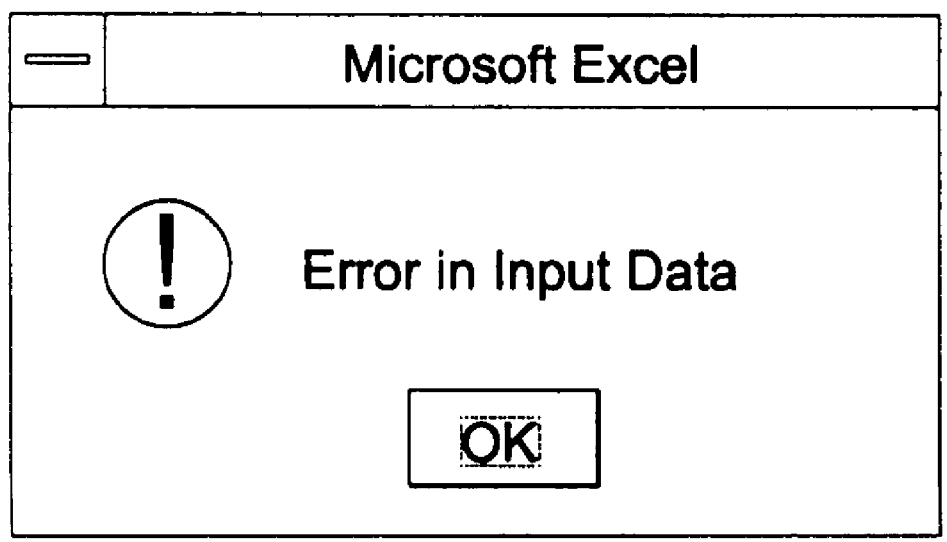
Figure 3F:
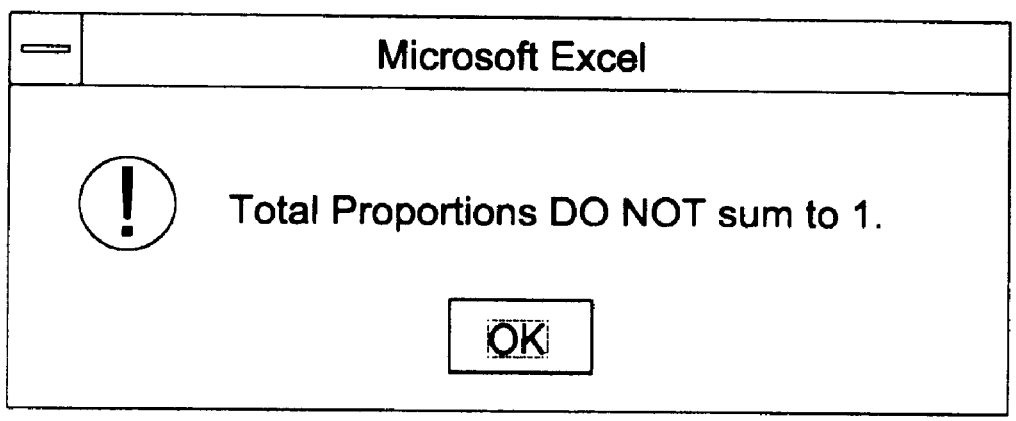
Figure 3G:
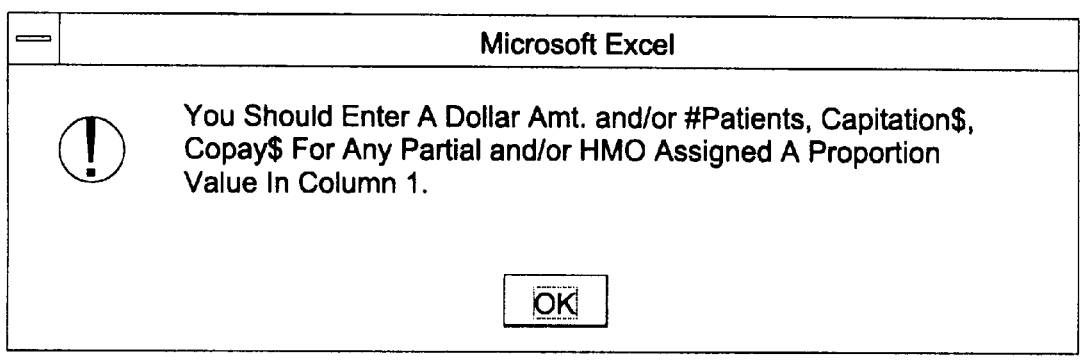
Figure 3H:
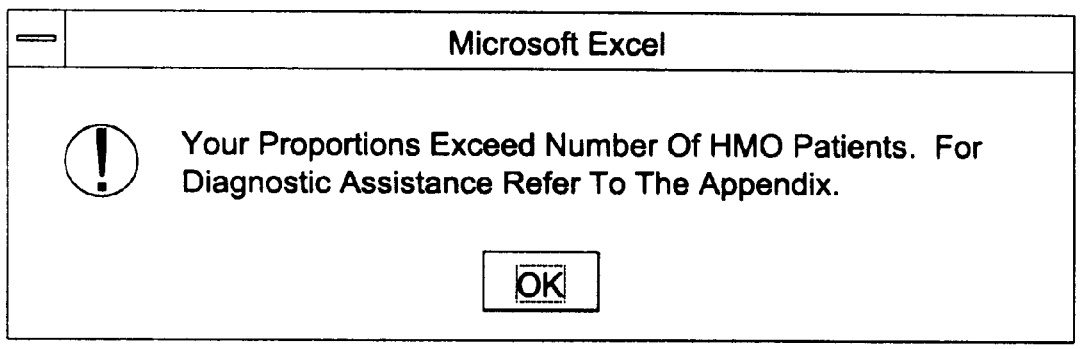
Figure 3I:
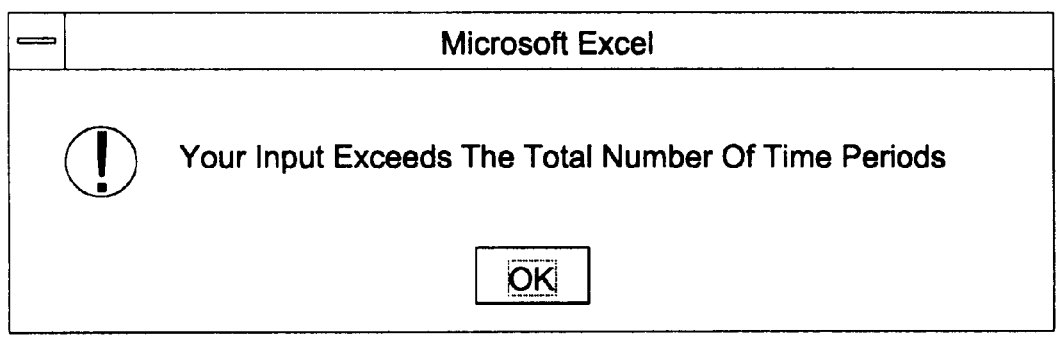

A typical embodiment of the use of PREMIN is illustrated in FIG. 2A through FIG. 2R. The first screen (FIG. 2A) welcomes the user to the program and marks the beginning of the program. This screen has no computational function. FIG. 2B and FIG. 2C are instruction screens and have no computational function. FIG. 2B instructs the program user on how to move within data input boxes. FIG. 2C instructs the program user about erroneous input data.

FIG. 2D marks the beginning of computational data input. Patient classification is used only for identification purposes. Patients can be classified in many different ways depending on "user" interest when approximating an FMI distribution. "User" specification of patient classification is flexible. Any patient category will typically consist of two or more patient classification characteristics. In the most general case, patients would comprise a single category, viz. "patients." Some examples of patient category classification are: age group, gender, type of illness. Base office visit charge is used in program computation to obtain the future minimum income. The charge represents base ambulatory office visit fee and should not include the cost of any medical procedures that may occur during the visit. The Total time period (TTI) screen (FIG. 2E) allows for entering the total time frame of interest for predicting FMI probability distributions and in practice will be specified but be variable (i.e., the interval of interest will be specified by the "user"). This value will typically be stated in terms of months. Any total time interval will be compared of successive time subintervals (TSI) of equal length. The maximum number of time periods allowed by the program is 60. The value entered must be integer. Each TSI is the source for basic input consisting of (1) Patient classification for all TSI
(2) Office visit probability distribution, L, M, H value, for any user-specified patient classification
(3) Sources of patient payments
(4) Base charges for sources of payments
(5) Proportion of patients in each source of payment category.

The number of office visits screen (FIG. 2F) is also a computational screen and allows for determination of FMI. Generally, the exact number of likely office visits in any time period is not known. The number of office visits screen allows for entering anticipated values of L, smallest number of possible visits, M, most probable number of visits, and H, largest number of possible visits. Source of payment proportions and additional data required in FIG. 2G concludes the computational screens for the program.

Source of payment refers to the source from which ambulatory patients fees are obtained by the physician. Only payments, and sources of such payment, for base office visit charges are considered. There are many sources of such payments.

Health insurance is provided by a variety of organizations, including private/commercial insurance, and managed care organizations. Organizations that provide managed care are called health maintenance organizations (HMO's). Preferred provider organizations (PPO's) are also referred to as managed care organizations.

Sources of payment are:
(1) Full compensation
(2) Partial compensation
(3) HMO (capitation) payment
(4) No compensation and are described as follows:
(1) Full compensation: Physician receives fill amount of stated fees.
(2) Partial compensation: Physician receives a partial amount of stated fees.
(3) HMO (Capitation) compensation: Physician receives a negotiated price per month per enrollee. This applies to enrollees who have selected a physician as primary care physician (PCP). The price received is commonly referred to as capitation payments. A PCP is one who serves as the "gatekeeper" for the patient's health care plan, and must approve many of the patient's health care needs, in addition to making referrals for consulting a specialist. The patient is usually responsible for a copayment per office visits.
(4) No compensation: Physician does not receive compensation for stated fees.

FIG. 2H allows the user to change or correct input. The mathematical an statistical foundation of the program is based on a method that determines the minimum number of independently distributed random variables required in a linear combination in order that its distribution can be approximated by the normal density function, i.e. normal approximation to linear combinations. For each TSI the following basic calculations are made:

1. Mean of triangular distribution $[\mu_1]$
2. Variance of triangular distribution $[\sigma_i^2]$
3. 3rd moment of triangular distribution $[\mu_{3i}]$
4. 4th moment of triangular distribution $[\mu_{4i}]$
5. Standardized 3rd moment of triangular distribution $[\alpha_{3i}]$ 6. Standardized 4th moment of triangular distribution [$\alpha_{4i}$]

7. Constants $c_i$ and K $$Y=K+c_1X_1+c_2X_2+\ldots+c_nX_n,$$

where $K=\Sigma K_i$ is a linear combination of $X_1, X_2, \ldots, X_n$. All $X_i$'s are assumed independent (i.e.. knowledge of the number of office visits that occur each month do not change probabilities associated with the number of office visits in previous or subsequent months). Further, specified data relating to sources of payment, etc. are used to determine the coefficients, $c_i$, associated with each $X_i$ and constants, $K_i$. The constant, $K_i$, is calculated using HMO number of patients and HMO capitation dollars for each TSI. This constant is independent of the random variable, $X_i$. The coefficients, $c_i$, are calculated from the required dollar amounts (i.e. HMO co-payment, Medicaid payment) per office visit for each TSI. The product, $c_iX_i$, is associated with income generation for a patient classification in a TSI. Summing incomes over two or more TSI and/or patient categories creates the linear combination of $X_i$'s. This linear combination, Y, will be for future minimum income. TVT then determines the FMI linear combination for total time interval, TTI. The following calculations are made:

1. Mean of the FMI linear combination $$E(Y)=\Sigma K_i+c_1\mu_1+c_2\mu_2+\ldots+c_n\mu_n.$$

2. Variance of the FMI linear combination $$V(Y)=c_1^2\sigma_1^2+c_2^2\sigma_2^2+\ldots+c_n^2\sigma_n^2.$$

3. 3rd moment of the FMI linear combination $$\mu_3(Y)=\Sigma a_i^3\mu_{3i}$$

4. 4th moment of the FMI linear combination $$\mu_4(Y)=\sum a_i^4\mu_{4i}+6\sum_{i=1}^{n-1}\sum_{j>i}^{n}a_i^2a_j^2\sigma_i^2\sigma_j^2$$

5. Standardized 3rd moment of the FMI linear combination $$\alpha_3(Y)=\frac{\sum a_i^3\mu_{3i}}{[\sum a_i^2\sigma_i^2]^{3/2}}$$

6. Standardized 4th moment of the FMI linear combination $$\alpha_4(Y)=\frac{\sum a_i^4\mu_{4i}+6\sum_{i=1}^{n-1}\sum_{j>i}^{n}a_i^2a_j^2\sigma_i^2\sigma_j^2}{[\sum a_i^2\sigma_i^2]^2}$$

7. $\text{Max}|c_i^3\mu_{3i}|$ {1}
8. $\text{Min}|c_i^3\sigma_i^3|$ {2}
9. $n_3=[\{1\}/\epsilon_3\{2\}]^2$
10. $\text{Max}|c_i^4\mu_{4i}|$ {3}
11. $\text{Min}|c_i^4\mu_{4i}^4|$ {4}
12. $\text{Max}|c_i^4\sigma_i^4|$ {5}
13. $\text{Min}|c_i^4\mu_{4i}|$ {6}
14. $n_4^+=[(\{3\}-3\{4\})/(\epsilon_4\{5\})]$
15. $n_4^-=[(3\{5\}-\{6\}]/(\epsilon_4\{5\})]$
16. $n_4=\text{Max}(n_4^+, n_4^-)$
17. $n^*=\text{Max}(n_3, n_4)$ TVT then determines the adequacy of normal approximation. If $n^*\leq TTI$, then normal approximation is adequate, Otherwise it is not adequate. When normal approximation is adequate the following calculations are performed:

1. Creation of the FMI normal distribution. This distribution is generated using the calculated mean and variance of the FMI linear combination.
2. Cumulative normal distribution of FMI
3. User-specified interval probabilities for FMI—. If normal approximation is not adequate then the program simulates the FMI distribution based on the input data, thereby generating a histogram of simulated FMI values and associated summary statistics such as a frequency distribution by count and percentages. When normal approximation is not adequate the following calculations are performed:

1. Monte Carlo simulation methods generate n number of office visit values for each TSI using the triangular distribution data L, M, H for each TSI.
2. Creation of n FMI values for TTI using TSI constants $c_i$, $K_i$, and n the generated number of office visit values.
3. Sample mean of the n FMI values.
4. Sample variance of the n FMI values.
5. Sample standard deviation of the n FMI values.
6. Sample 3rd moment of the n FMI values.
7. Sample 4th moment of the n FMI values.
8. Standardized 3rd moment of the n FMI values.
9. Standardized 4th moment of the n FMI values.
10. Difference, $\epsilon_3$, between standardized 3rd moment of the n FMI values and the value "0."
11. Difference, $\epsilon_4$, between standardized 4th moment of the n FMI values and the value "3."

The value arbitrarily selected for $\epsilon_3$ and $\epsilon_4$ is 0.15 in the prototype version of the computer system. This could be a user-specified input in an expanded version of the computer system. FIG. 2I to FIG. 2N are screens associated with cases when normal approximation is adequate and FIG. 2O to FIG. 2R are screens associated with cases when normal approximation is not adequate.

FIG. 2I shows the screen that notifies the user that normal approximation is adequate and allows the user to ask the program for cumulative probabilities for an FMI of interest. That is, obtain the probability of FMI being less than or equal to the user's FMI of interest. FIG. 2J allows for entering the FMI of interest. FIG. 2K allows the user to repeat the activity for any FMI of interest. FIG. 2L allows the user to obtain mean (average) plus and minus sigma (standard deviation) values. FIG. 2M allows the user to print the normal density curve of FMI values. FIG. 2N reminds the user to check the printer for power and paper. FIG. 2O informs the user that a normal density curve of FMI values can not be approximated based on data entered. A histogram will be generated. FIG. 2P asks the user to enter the number or time periods for the histogram. The input must be numeric and must not exceed total number of time periods entered in FIG. 2E. FIG. 2Q allows the user to see summary statistics such as mean, variance, other moments. FIG. 2R allows the user to generate another histogram.

Operation—FIGS. 1, 2, 3

The manner of using the PREMIN program is as follows:
1. Open Microsoft EXCEL.
2. Select FILE from the EXCEL toolbar (this is done by putting the pointer on FILE and clicking the left button on the mouse).
3. Select OPEN (this is done by putting the pointer on OPEN and clicking the left button on the mouse).
4. Type TVT.XLM or select TVT.XLM from the list of files in the file menu (this is done by putting the pointer on the arrow pointing down, holding down the left button on the mouse until the file TVT.XLM appears in the menu box, put the pointer on the desired file and double click the left button on the mouse).
5. Click on cell A1 (this is done by putting the pointer on cell A1 and clicking the left button on the mouse).
6. Select TOOLS from the toolbar.
7. Select MACRO.
8. Select RUN.
9. You will see an information box Welcome to PREMIN. (FIG. 2A) Click on "OK" or press "Enter."
10. You will see an information box (FIG. 2B) informing you to use the Tab key to move within input boxes. Click on "OK" or press "Enter."
11. You will see an information box (FIG. 2C) informing you to BEWARE of inputting blank answers in PREMIN. Blank answers where numeric input is expected may result in an error message "Error In Formula." (FIG. 3A) If you get this message you must restart PREMIN i.e., Go to Step 1.

Figure 1A:
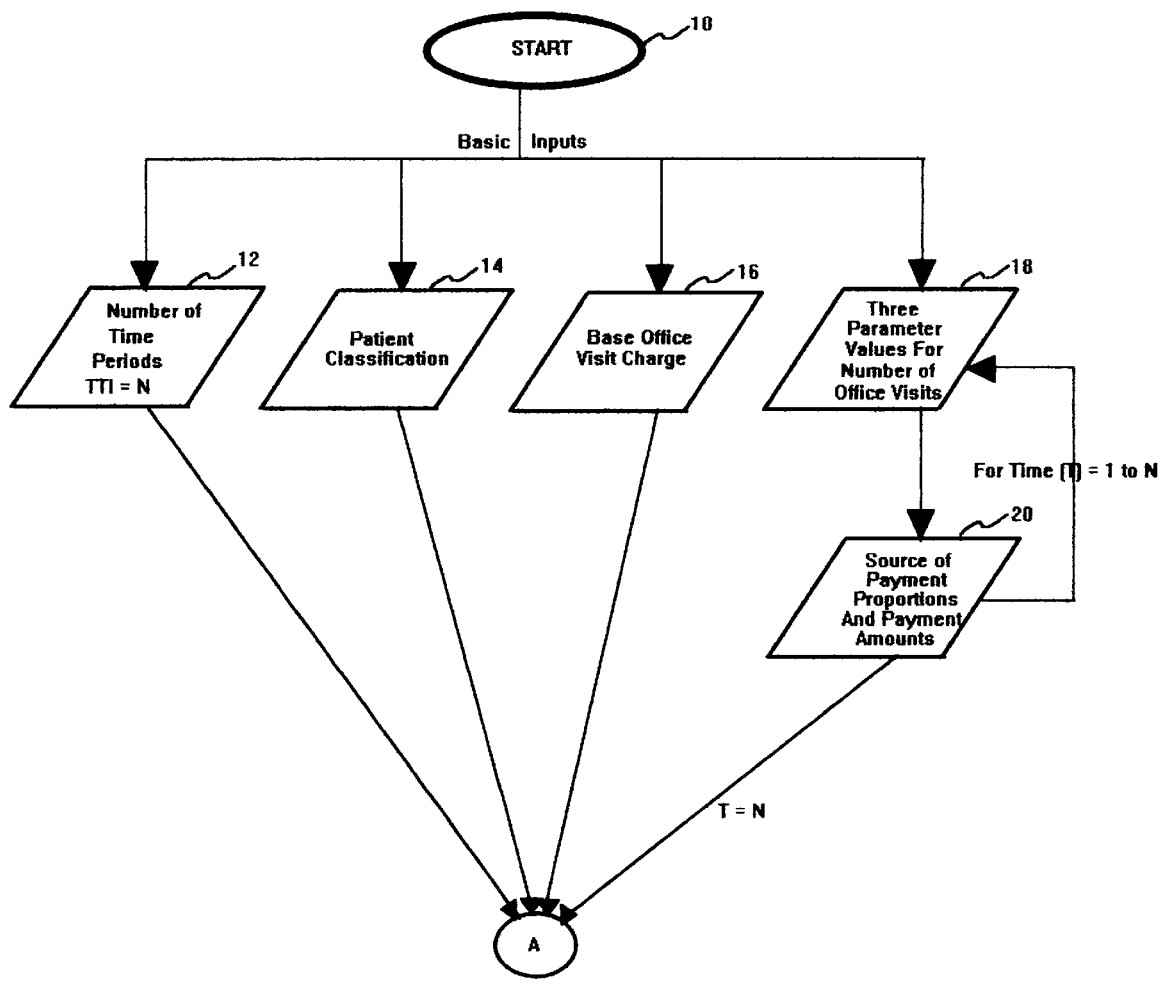
FIGS. 1A to 1C show a general flow diagram of the computerized future minimum income (FMI) prediction system, PREMIN (PREdictor of Minimum INcome).

Referring to FIG. 1A, the interactive program begins at start block 10 and proceeds to first input block 12 then to remaining input blocks 14, 16, 18, 20.

12. You will be asked to enter Patient Classification and Base Office Visit Charge (FIG. 2D). Don't forget to use the Tab key to move within the input box.

Patient Classification must be a single group of patients. It can be males age 25–50, females, age group 45–65, etc. The input can be alphanumeric.

Base Office Visit Charge must be a single value. This value does not include the cost of any medical procedures that may occur during the visit.

The input must be numeric. If input is not numeric you will get an EXCEL error message "Number Is Not Valid." (FIG. 3B) You will be given two options (1) "OK" or (2) "Help." If you click on "Help" an EXCEL Help Message Box will open and inform you that your input should be integer or a decimal number. Select FILE (from Help Message Box toolbar). Select EXIT. The error message box ("Number Is Not Valid.") (FIG. 3B) will reappear. Click on "OK." The cell where the error occurred will be highlighted. Enter a numeric value for base office visit charge. Press "Enter."

13. You will be asked to enter Total Number of Time Periods. (FIG. 2E) The time periods should be of equal lengths, i.e., all weeks or all months or all days, etc. This value must be integer. The maximum number of time periods currently allowed is 60.

If input is not integer you will get an EXCEL error message "Integer is not valid." (FIG. 3C) You will be given two options (1) "OK" or (2) "Help." If you click on "Help" an EXCEL Help Message Box will open and inform you that your input should be integer. elect FILE (from Help Message Box toolbar). Select EXIT. The error message box ("Integer Is Not Valid.") (FIG. 3C) will reappear. Click on "OK." The Total Time Period input box will reappear. The cell where the error occurred will be highlighted. Enter an integer value for total number of time periods. Press "Enter."

If input value exceeds 60 you will get an error message "Maximum Total Time Periods Is 60." (FIG. 3D) Click on "OK" or press "Enter." The Total Time Period input box will reappear. Enter a corrected integer value (<61) for total number of time periods. Press "Enter."

14. You will be asked to enter three values (L, M, H) to represent the anticipated number of office visits for a single time period. Remember to use the Tab key to move within the input box. Enter a single value for L, M, and H. (FIG. 2F)

(a) You will be informed that these values must be integer. If input is not integer you will get an EXCEL error message "Integer is not valid." (FIG. 3C) You will be given two options (1) "OK" or (2) "Help." If you click on "Help" an EXCEL Help Message Box will open and inform you that your input should be integer. Select FILE (from Help Message Box toolbar). Select EXIT. The error message box ("Integer is not valid") (FIG. 3C) will reappear. Click on "OK." The Office Visits input box will reappear. The cell where the error occurred will be highlighted. Enter the correct integer value for L and/or M and/or H. Press "Enter."

(b) You will be informed that $L<M<H$ or $L=M<H$ or $L<M=H$. If you violate these constraints you will get an error message "Error in input data." (FIG. 3E) Click on "OK" or press "Enter." The Office Visits input box will reappear. Make sure that one of the conditions ($L<M<H$ or $L=M<H$ or $L<M=H$) is true. Locate the error. Type the correct value for L and/or M and/or H. Press "Enter."

(c) You will be asked if the data you entered is correct. (FIG. 2H) You will be informed that if you answer "Yes" you will not have another opportunity to change the data. Please make sure the data you entered is correct! You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter." If you type "Yes" in the answer box you must use the same upper/lower case letters as the default. The program recognizes any other entry as "No." If you answer "No" (i.e., clicking on "Cancel" or typing "No," or anything other than "Yes," in the answer box), the Office Visits input box will reappear. Type the desired changes in L and/or M and/or H. Press "Enter."

15. You will be asked to enter Source of Payment Proportions and Additional Data (FIG. 2G) for a single time period. Full represents full payment received, i.e. the total base office visit charge. Partial represents partial payment received as with Medicaid. HMO represents health maintenance organization arrangement. None represents no payment received. Remember to use the Tab key to move within the input box.

(a) You will be instructed to enter proportions in decimal format, i.e. 0.12, 0.05, etc., in the first column. The value 1 may be entered without decimal format. Proportions must sum to 1. If proportions do not sum to 1 you will get an error message "Total proportions DO NOT sum to 1." (FIG. 3F) Click on "OK" or press "Enter." The Source of Payment Proportions and Additional Data input box will reappear. Locate the error. Enter the correct proportion value. Press "Enter."

(b) You will be informed that all dollar amounts must be numeric. If input is not numeric you will get an EXCEL error message "Number is not valid." (FIG. 3B) You will be given two options (1) "OK" or (2) "Help." If you click on "Help" an EXCEL Help Message Box will open and inform you that your input should be integer or a decimal number. Select FILE (from Help Message Box toolbar). Select EXIT. The error message box ("Number is not valid.") (FIG. 3B) will reappear. Click on "OK." The cell where the error occurred will be highlighted. Enter a numeric value for dollar amount. Press "Enter."

(c) You will be informed that all HMO number of patients must be integer. If input is not integer you will get an EXCEL error message "Integer is not valid. (FIG. 3C) You will be given two options (1) "OK" or (2) "Help." If you click on "Help" an EXCEL Help Message Box will open and inform you that your input should be integer. Select FILE (from Help Message Box toolbar). Select EXIT. The error message box ("Integer is not valid.") (FIG. 3C) will reappear. Click on "OK." The Source of Payment Proportions and Additional Data input box will reappear. The cell where the error occurred will be highlighted. Enter an integer value for HMO number of patients. Press "Enter."

(d) You must enter a dollar amount for any partial source assigned a proportion value in column 1. You must also enter a value for number of patients, capitation dollar amount, copay dollar amount for any HMO source assigned a proportion value in column 1. If you do not enter a dollar amount and/or value for number of patients, capitation dollar amount, copay dollar amount you will get an error message "You Should Enter A Dollar Amount And/Or #Patients, Capitation$, Copay$ For Any Partial And/Or HMO Assigned a Proportion Value in Column 1". (FIG. 3G) Click on "OK", or press "Enter." The Source of Payment Proportions and Additional Data input box will reappear. Locate the error. Enter dollar amount and/or value for number of patients, capitation dollar amount, copay dollar amount. Press "Enter."

(e) The proportion x (L), proportion x (M), or proportion x (H) should not exceed the number of patients for any HMO. Capitation dollars are received for the entered number of patients. If proportion x (L), or proportion x (M), or proportion x (H) exceeds number of patients entered, the physician/health facility will not have received capitation dollars for some patients. If this constraint is violated you will get an error message "Your proportions exceed number of HMO patients. For Diagnostic Assistance Refer To The Appendix. (FIG. 3H) Click on "OK", or press "Enter." The Source of Payment Proportions and Additional Data input box will reappear. Locate the error. Enter correct proportions and/or number of patients. Press "Enter."

If you discover you have entered incorrect values for L, M, or H, you MUST RESTART THE PROGRAM AND CORRECT THE ERROR(S) AS DESCRIBED IN STEP 14(c).

(f) You will be asked if the data you entered is correct. You will be informed that if you answer "Yes" you will not have another opportunity to change the data. Please make sure the data you entered is correct! (FIG. 2H) You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter." If you type "Yes" in the answer box you must use the same upper/lowercase letters as the default. The program recognizes any other entry as "No." If you answer "No" (i.e., clicking on "Cancel" or typing "No," or anything other than "Yes," in the answer box), the Source of Payment Proportions and Additional Data input box will reappear. Type the desired changes in proportions and/or additional data. Press "Enter."

16. Repeat steps 14 and 15 for each time period, TSI. The current time period will be displayed in the lower left corner of the screen. The time period is updated after source of payment data is entered.

Time period entries for L, M, H and source of payment will reappear in the input boxes for subsequent time periods and can be duplicated as input by pressing "Enter" or clicking "OK."

Figure 1B:
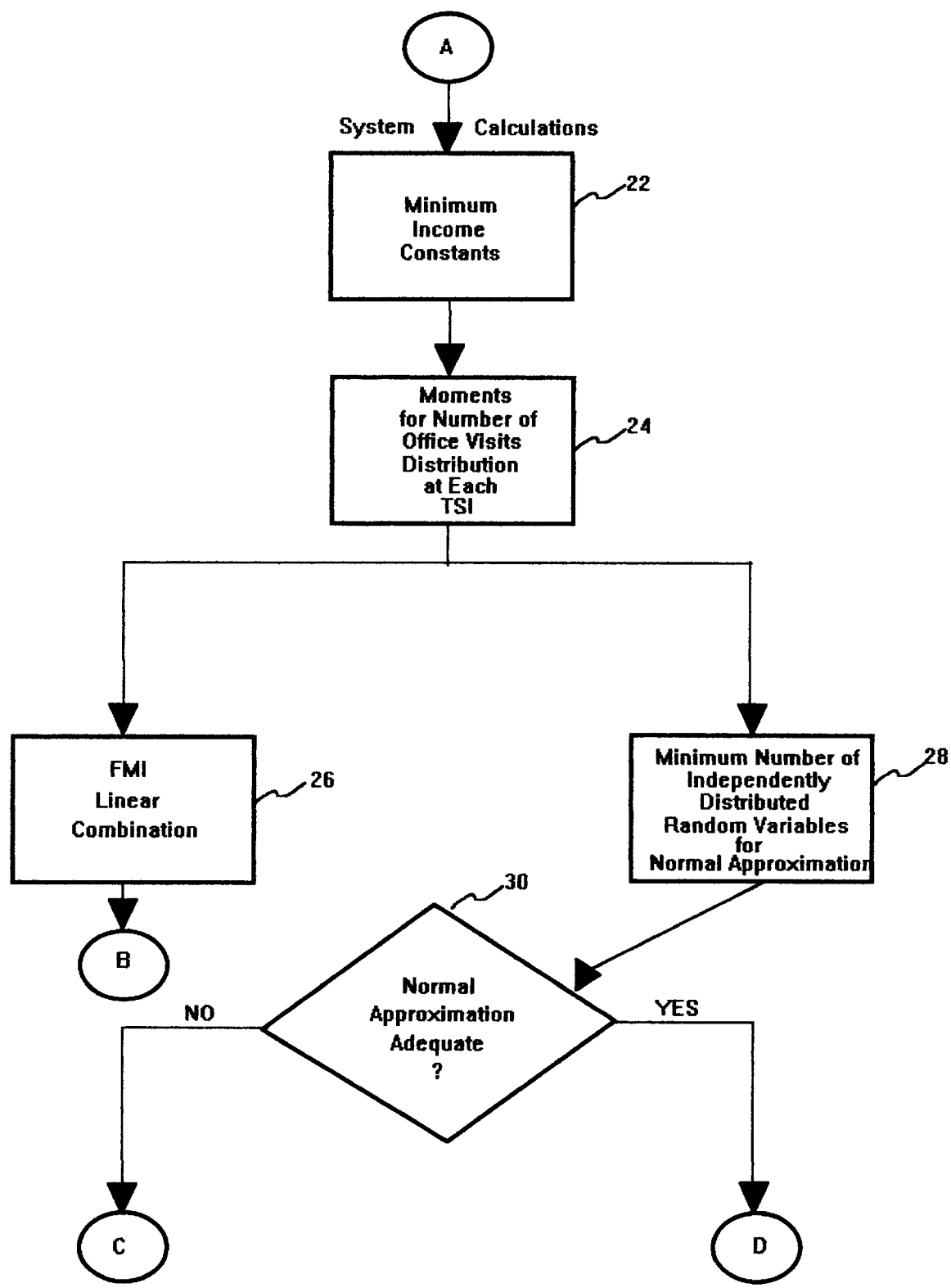

Referring to FIG. 1B, PREMIN calculations begin at Minimum Income Constants block 22 proceeds to FMI Linear Combination block 26 and Minimum Number of Independently Distributed Random Variables for Normal Approx. block 28 then advances to a decision block 30.

PREMIN will determine, based on your input, (1) The FMI probability distribution approximated by the Normal Distribution (Normal Approximation is Adequate) or (2) Normal Approximation is not adequate.

Normal Approximation Is Adequate

Referring to FIG. 1, PREMIN proceeds to output block FMI Distribution 36. The interactive program advances to STOP block 42.

17. You will be informed that FMI can be approximated by the Normal Distribution. (FIG. 2I)

(a) You will be asked if you would like to obtain the cumulative probability of an FMI of interest. (FIG. 2I) This is the same as obtaining the probability that FMI will be less than or equal to the FMI of interest. You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter." If you type "Yes" in the answer box you must use the same upper/lower case letters as the default. The program recognizes any other entry as "No."

[i] If you answer "No" (i.e., clicking on "Cancel" or typing "No," or anything other than "Yes," in the answer box) the program will automatically generate the FMI probability distribution. Go to Step 17 (c).

[ii] If you answer "Yes" (i.e., click on "OK," or press "Enter") you will be asked to enter the FMI of interest. This input must be numeric. Enter a numeric value. Press "Enter." Go to Step 17 (b).

If input is not numeric you will get an EXCEL error message "Number is not valid." (FIG. 3B) You will be given two options (1) "OK" or (2) "Help." If you click on "Help" an EXCEL Help Message Box will open and inform you that your input should be integer or a decimal number. Select FILE (from Help Message Box toolbar). Select EXIT. The error message box ("Number is not valid.") (FIG. 3B) will reappear. Click on "OK." The cell where the error occurred will be highlighted. Enter a numeric value for FMI of interest. Press "Enter."

(b) You will be informed that the cumulative probability of the FMI you entered is shown below the message box. (FIG. 2K) You will be asked if you would like to enter another FMI of interest. There is no limit to the number of inquiries into the cumulative probability for FMI. You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter." If you type "Yes" in the answer box you must use the same upper/lower case letters as the default. The program recognizes any other entry as "No." See Step 17 (a) parts [i] and [ii].

(c) You will be asked if you would like to see Mean +/− Sigma values. (FIG. 2L) You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter." If you type "Yes" in the answer box you must use the same upper/lower case letters as the default. The program recognizes any other entry as "No."

[i] If you answer "No" (i.e., clicking on "Cancel" or typing "No," or anything other than "Yes," in the answer box) go to Step 19.

[ii] If you answer "Yes" (i.e., click on "OK," or press "Enter") the Mean +/− Sigma values will appear in a highlighted box on the left side of your screen. It may be necessary to scroll down in order to see all the values. This is done by clicking on the arrow pointing down box located in the bottom right corner of the screen. Go to Step 19.

Normal Approximation Is Not Adequate

Figure 1C:
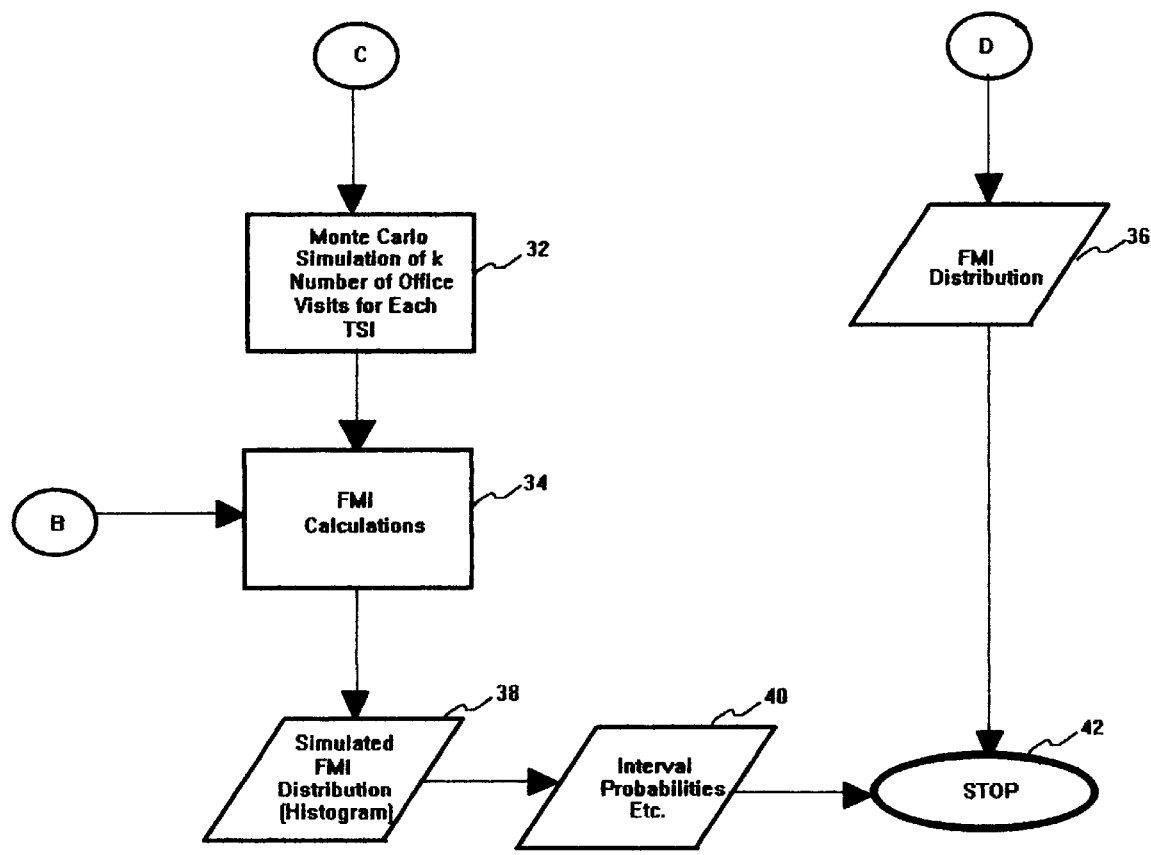

Referring to FIG. 1C, PREMIN proceeds to calculation block Monte Carlo Simulation of k Number of Office Visits for Each TSI 32 and FMI Calculations block 34 and advances to output blocks 38, 40. The interactive program advances to STOP block 42.

18. You will be informed that FMI cannot be approximated by the Normal Distribution and that a histogram will be generated. (FIG. 2O) Press "Enter."

(a) You will be asked to enter the number of time periods for the histogram (starting with time period 1). (FIG. 2P) This input should be integer and must not be greater than the total number of time periods. Enter an integer value less than or equal to the total number of time periods. Press "Enter."

If input is not integer you will not get an error message. However, EXCEL will ignore the decimal and generate a histogram based on the number before the decimal.

If input exceeds the user-specified total number of time periods you will get an error message "Your Input Exceeds User-Specified Total Number Of Time Periods." (FIG. 3I) Click on "OK" or press "Enter." The Number Of Time Periods For Histogram input box will reappear. Enter a corrected value (less than or equal to user-specified total number of time periods). Press "Enter."

(b) You will be asked if you would like to print the graph. (FIG. 2M) You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter."

If you type "Yes" in the answer box you must use the same upper/lower case letters as the default. The program recognizes any other entry as "No."

[i] If you answer "No" (i.e., clicking on "Cancel" or typing "No," or anything other than "Yes," in the answer box) go to Step 18 (c).

[ii] If you answer "Yes" (i.e., click on "OK," or press "Enter") you will be asked to make sure the printer is on and paper is loaded. (FIG. 2N) Press "Enter." The graph will be printed. Go to Step 18 (c).

(c) You will be asked if you would like to view summary statistics. (FIG. 2Q) You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter." If you type "Yes" in the answer box you must use the same upper/lower case letters as the default. The program recognizes any other entry as "No."

[i] If you answer "No" (i.e., clicking on "Cancel" or typing "No," or anything other than "Yes," in the answer box). Go to Step 18 (d).

[ii] If you answer "Yes" (i.e., click on "OK," or press "Enter") you will see the first, second, third, and fourth moments of the FMI distribution in a highlighted box on the right side of your screen. It may be necessary to scroll right in order to see all the values. This is done by clicking on the arrow pointing right box located in the bottom right corner of the screen. Go to Step 18 (d).

(d) You will be asked if you would like to generate another histogram. (FIG. 2R) You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter." If you type "Yes" in the answer box you must use the same upper/lower case letters as the default. The program recognizes any other entry as "No."

[i] If you answer "No" (i.e., clicking on "Cancel" or typing "No," or anything other than "Yes," in the answer box), go to Step 20.

[ii] If you answer "Yes" (i.e., click on "OK," or press "Enter"), go to Step 18 (a).

19. You will be asked if you would like to print the graph (FMI distribution). (FIG. 2M) You will be given two options (1) "OK" (Yes) or (2) "Cancel" (No). You may click on "OK" or "Cancel." The default answer, "Yes," will be seen in the answer box. Therefore, you also may press "Enter" to answer "Yes" or you may type "No" in the answer box then press "Enter." If you type "Yes" in the answer box you must use the same upper/lower case letters as the default. The program recognizes any other entry as "No."

(a) If you answer "No" (i.e., clicking on "Cancel" or typing "No," or anything other than "Yes," in the answer box)all worksheets will close. Select FILE. Select EXIT. The program will terminate.

(b) If you answer"Yes" (i.e., click on "OK," or press "Enter") you will be asked to make sure the printer is on and paper is loaded. (FIG. 2N) Press "Enter." The graph will be printed. All worksheets will close. Select FILE. Select EXIT.

(c) You will be asked if you want to save the chart. If you answer "Yes" you must type a file name for the chart then press "Enter." The program will terminate. If you answer "No" the program will terminate.

20. You will be asked if you would like to save changes in a file (worksheet). DO NOT SAVE!

(a) Click on "No".

(b) Repeat Step 20 (a) for all files (worksheets).

21. Exit EXCEL (1. Click on the box with a horizontal bar located in the top left corner of your screen, Select CLOSE or 2. Select FILE from the toolbar, Select EXIT)

SUMMARY RAMIFICATIONS, AND SCOPE

The program user will see that PREMIN is a useful tool for predicting future minimum income. In addition, the program can provide vital and beneficial financial data to health care facilities. Further, the invention has the additional advantages in that it provides a method that predicts probability distributions of health care facility future minimum income superior to any existing methods;

it allows for estimation of anticipated number of ambulatory office visits with three simple values L, M, H;

it allows for speculation of proportion of payment services it provides a plot of the normal probability density function (the bell-shaped curve) for future minimum income distribution and associated cumulative probabilities;

it provides a histogram of simulated future minimum income values and associated summary statistics (frequency distribution by count and percentages);

it is transportable to other computers.

Although the description above contains many specificities, these should not be construed as limiting the scope of PREMIN but as merely providing illustrations of some of the present embodiment of PREMIN. For example, PREMIN can be expanded to allow the user to save and re-run scenarios without re-entering the data and other options and features that can be added to the program to further enhance the appearance and "user-friendliness."

Thus the scope of PREMIN should be determined by the appended claims and their legal equivalents, rather than by the examples given.

I claim:

1. An interactive method of using a computer processor to execute a computer program comprising a plurality of formulas for predicting a probability distribution of a health care facility predicted future minimum income for a total time interval, the method comprising the steps of:

(a) inputting into the computer program a patient category classification, (b) inputting into the computer program a base office visit charge, (c) inputting into the computer program a total number of equal length time periods, (d) inputting into the computer program a value for the smallest number of possible office visits for a single time period, a value for the most probable number of possible office visits for a single time period and a value for the largest number of possible office visits for a single time period, (e) inputting into the computer program a proportion of patients in each category of payment sources, the categories of payment sources consisting of full compensation, partial compensation, Health Maintenance Organization payment and no compensation, (f) determining the minimum number of independently distributed random variables required in a linear combination of future maximum income in order for a prediction of health care facility future minimum income distribution to be approximated by a normal density function, (g) examining the result of said formulas whereby the program determines the adequacy of a plot of the normal density function for predicting health care facility future minimum income probability distributions, and, (h) translating the result of said formulas whereby the computer determines future minimum income for the health care facility and prints a normal density function plot of the health care facility future minimum income.

2. The method of claim 1, wherein formula results are examined by a technique of normal approximation to linear combinations.

3. The method of claim 1, whereby the computer program provides a histogram of simulated health care facility future minimum income values and associated summary statistics upon a determination by the computer program that a plot of the normal density function for predicting health care facility future minimum income probability distributions is not adequate.

* * * * *